US00PP26186P3

(12) United States Plant Patent
Lucci et al.

(10) Patent No.: US PP26,186 P3
(45) Date of Patent: Dec. 1, 2015

(54) ***PETUNIA* PLANT NAMED 'DRAMA QUEEN'**

(50) Latin Name: *Petunia hybrida*
Varietal Denomination: Drama Queen

(71) Applicant: Skagit Gardens, Inc., Mount Vernon, WA (US)

(72) Inventors: Laura Laloma Lucci, Anacortes, WA (US); Gina Falcetti, Sedro Woolley, WA (US)

(73) Assignee: Skagit Gardens, Inc., Mount Vernon, WA (US)

( * ) Notice: Subject to any disclaimer, the term of this patent is extended or adjusted under 35 U.S.C. 154(b) by 203 days.

(21) Appl. No.: 13/998,612

(22) Filed: Nov. 14, 2013

(65) Prior Publication Data

US 2015/0135383 P1 May 14, 2015

(51) Int. Cl.
*A01H 5/00* (2006.01)

(52) U.S. Cl.
USPC ..... Plt./356.16

(58) Field of Classification Search
USPC ..... Plt./356.16
See application file for complete search history.

*Primary Examiner* — Annette Para
(74) *Attorney, Agent, or Firm* — Klarquist Sparkman, LLP

(57) ABSTRACT

A new *Petunia* variety distinguished by its strong, stable variegated foliage with a flower color and habit unseen in previously existing *petunia* clones.

5 Drawing Sheets

Latin name of the genus and species of the plant claimed: *Petunia hybrida.*

Variety denomination: 'Drama Queen'.

BACKGROUND

The present application relates to a new and distinct variety of *petunia* named 'Drama Queen'. 'Drama Queen' is a chance seedling from a group of mixed colored *petunias* of various origin (an open pollenated mix) discovered in Mount Vernon, Wash. Seed and pollen parents are unknown.

The 'Drama Queen' variety is distinguished from other *petunia* varieties due to its strong, stable variegated foliage with a flower color and habit unseen in previously existing *petunia* clones (for example see FIG. 3).

Asexual reproduction of this new variety was achieved in Mount Vernon, Wash., using tip and stem cutting from vegetative stock plants.

Certain characteristics of this variety may change with changing environmental conditions (such as photoperiod, temperature, moisture, soil conditions, nutrient availability, or other factors). Color descriptions and other terminology are used in accordance with their ordinary dictionary descriptions, unless the context clearly indicates otherwise. Color designations (hue/value/chroma) are made with reference to The Royal Horticultural Society Colour Chart (R.H.S.).

Figure 1:
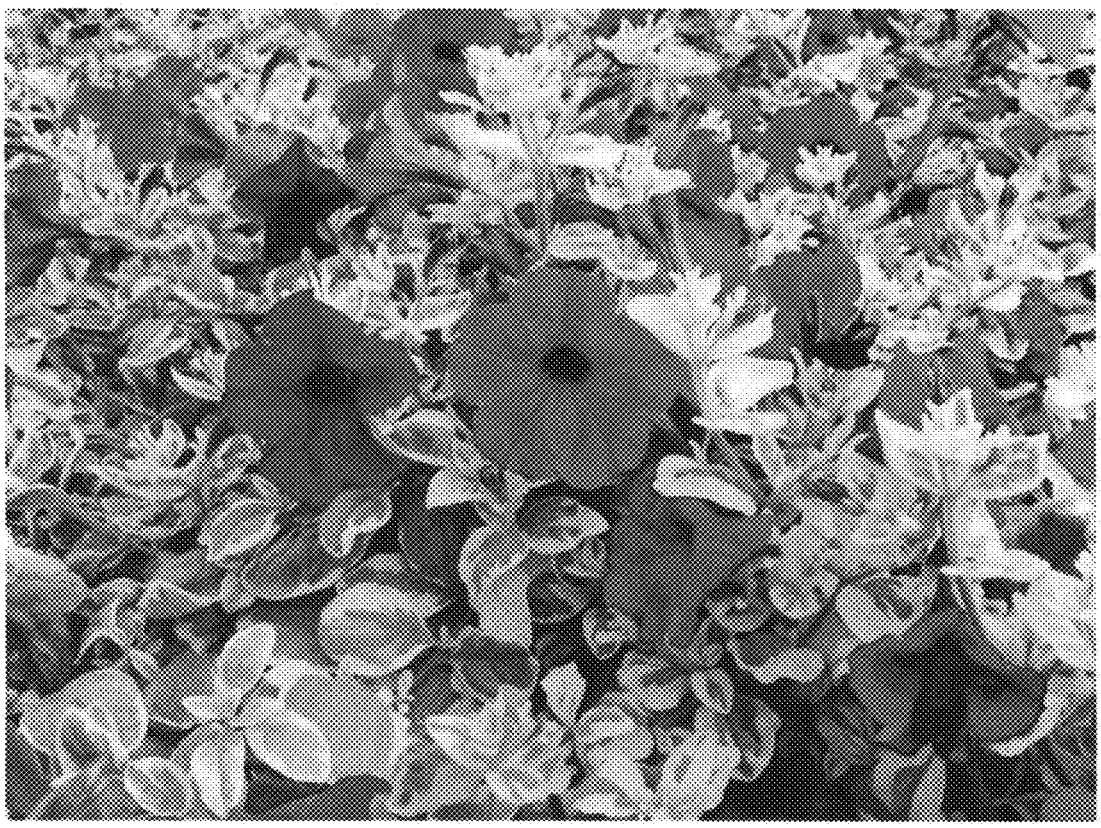
FIGS. 1 and 2 are photographs showing the new variety 'Drama Queen' taken in June and October 2013, respectively.
Figure 2:
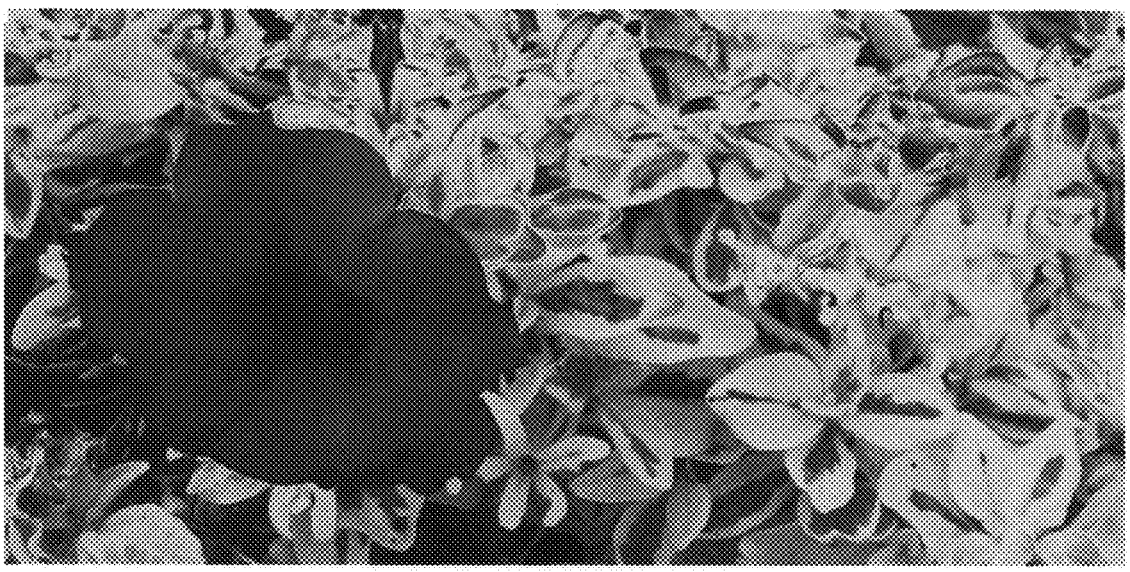
Figure 3:
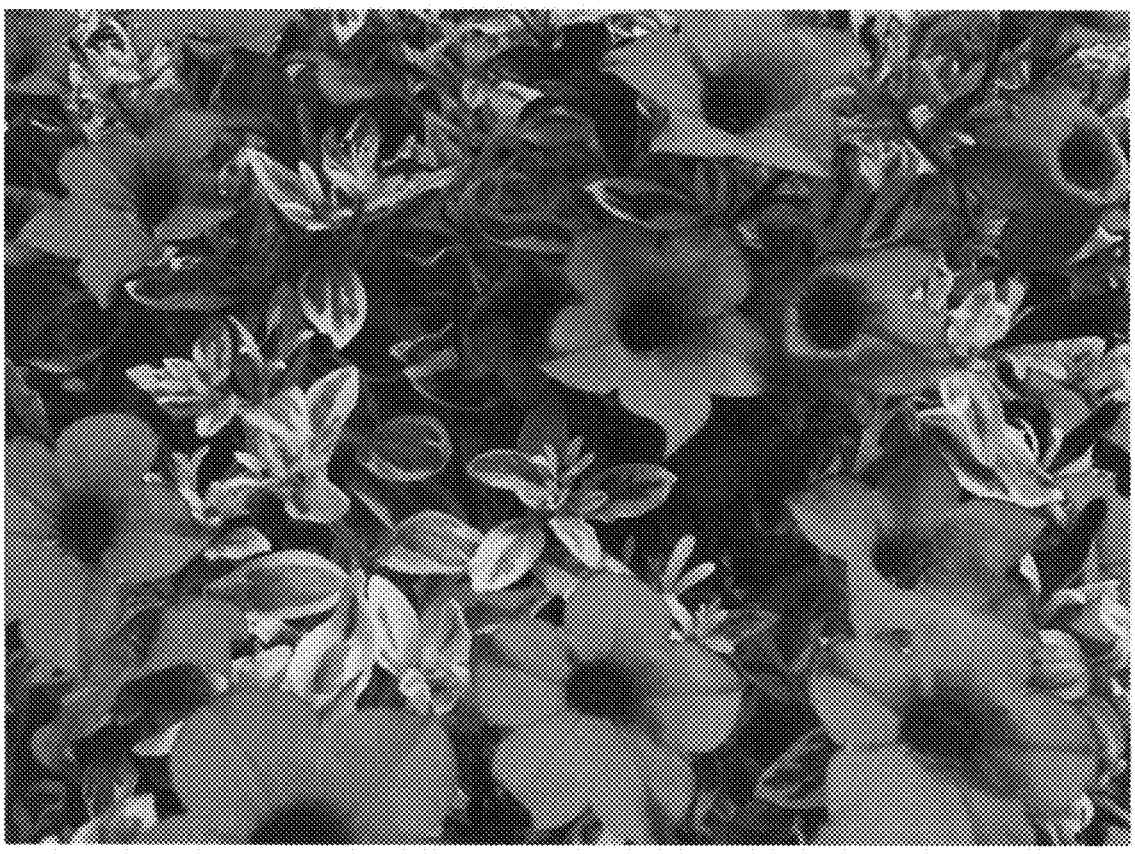
FIG. 3 is a photograph showing the variety 'Glamouflage Grape'.
Figure 4:
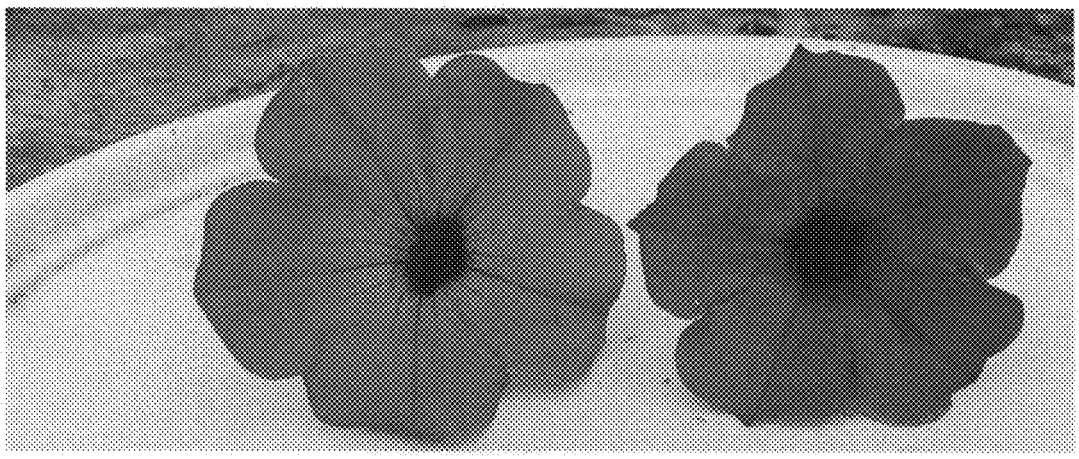
FIG. 4 is a photograph comparing the flowers of the variety 'Glamouflage Grape' (left) and the new variety 'Drama Queen' (right).
Figure 5:
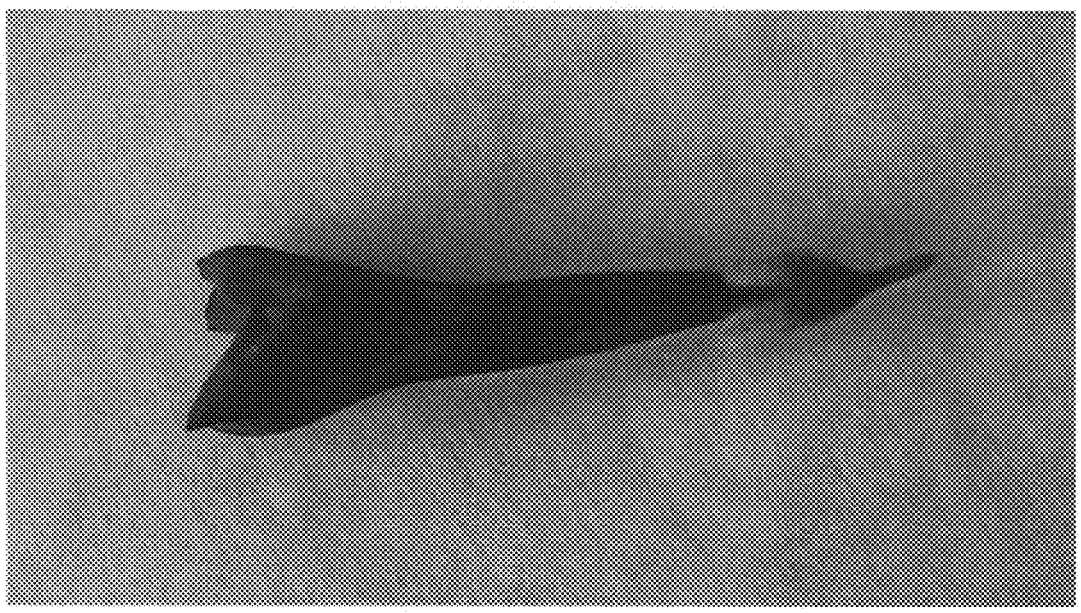
FIGS. 5 and 6 are photographs showing the side of the immature and mature flower, respectively, of the new variety 'Drama Queen'.
Figure 6:
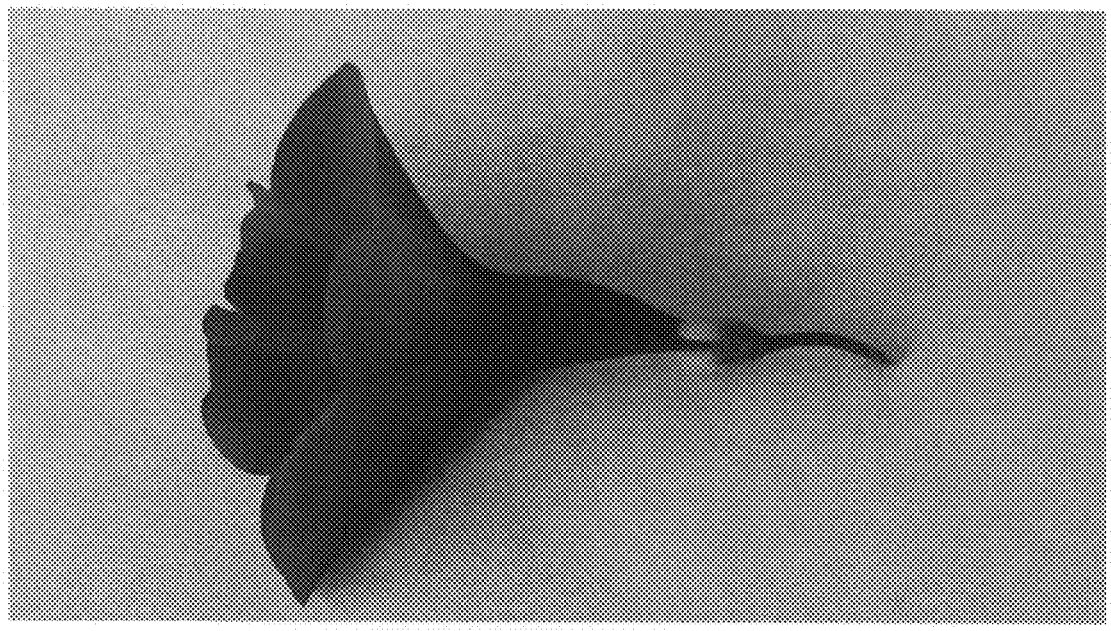
Figure 7:
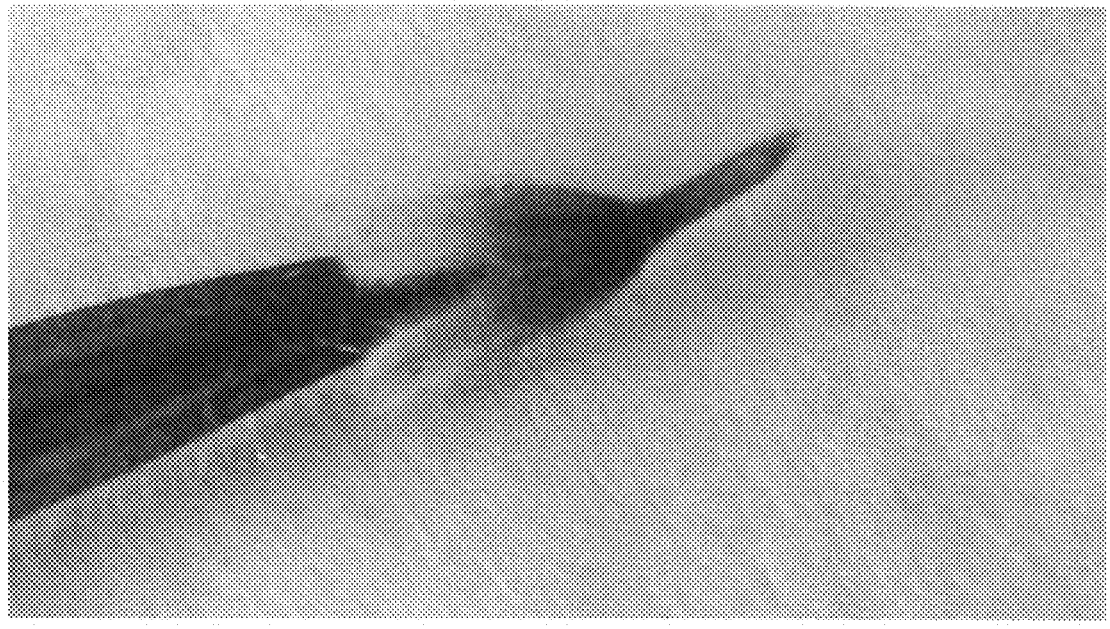
FIG. 7 is a photograph showing the calyx of the new variety 'Drama Queen'.

The color photographs show typical specimens of the plant; structure and form, leaf color and flower color, and an overall comparison to existing clones on the NAFTA market. The color photographs shows typical specimens and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

The following detailed description of the 'Drama Queen' variety is based on observations of asexually reproduced progeny. The observed progeny are plants which were 1 to 45 weeks of age. The following detailed description concerns the plants growing in open ground, (sandy loam), in full sun, (southern exposure) in La Conner, Wash., between Mar. 17, 2013 and Oct. 4, 2013. The original plant and progeny have been observed growing in a cultivated area Mount Vernon, Wash.

The chart used in the identification of colors described herein is The R.H.S. Colour Chart of The Royal Horticultural Society, London, England, 2001 edition, except where general color terms of ordinary significance are used. The color values were determined in July and August 2013 under natural light conditions in La Conner, Wash.

Scientific name: *Petunia*×'Drama Queen'.

Plant:

*Form, growth and habit.*—Spreading/prostrate habit with upward and outward facing inflorescence.

*Plant height.*—5 cm to 10 cm.

*Plant height* (*inflorescence included*).—10 to 20 cm.

*Plant width.*—60 cm to 120 cm.

*Rooting.*—Number of days to initiate roots 5 to 10, and 15 to 21 days to produce a 10×20, 105 cell.

Leaves:

*Type.*—Obovate.

*Color.*—Variegated.

*Foliage.*—Arrangement. alternate.

*Immature, leaf color.*—Upper surface, RHS outer 50 to 70% 11D/inner 30 to 50% 138B; Lower surface, RHS same as upper.

*Mature, leaf color.*—Upper surface, same as Immature.

*Length.*—3 cm to 4 cm.

*Width.*—1.5 cm to 2 cm.

*Shape.*—Obovate. Base shape. rounded. Apex shape. acute.

*Margin.*—Entire.

*Texture.*—Upper and lower surface is sticky, finely prunose.

*Color of veins on upper and lower surface.*—Undeterminable, masked by variegation.

*Petiole.*—Color. RHS outer 50 to 70% 11D/inner 30 to 50% 138B. Length. 3 cm to 4 cm; Diameter.1 mm to 2 mm; Texture. same as leaf.

*Stem.*—Color of stem. RHS 11D. Length of stem. 40 cm to 70 cm. Diameter. 2 mm to 4 mm. Length of internodes 1 cm to 5 cm. Texture. Same as foliage.

*Color of peduncle.*—RHS 11D.

*Length of peduncle.*—2 cm to 3 cm.

*Peduncle diameter.*—1 cm to 2 mm.

*Texture.*—Consistent with other plant structure.

Flowers:

*Size.*—Length, 4 cm to 6 cm; width 4 cm to 4.5 cm.

*Shape.*—Solitary trumpet.

*Color.*—Unopened bud: RHS N89D in color Opened flower: RHS N89D in color.

*Petals.*—5 petals per flower; trumpeted in shape; 3 cm to 5 cm in length. N89D in color.

*Stamen.*—5 in number, 1 cm to 2 cm in length.

*Anthers.*—96B in color, 1 mm to 2 mm in length.

*Pistil.*—Stigma is about 3 mm long; tubular/oval in shape; single styles, and 149C in color.

*Sepals.*—About 5 mm long and about 2 mm wide (at base); oblong in shape; variegated as foliage in color.

*Inflorescence.*—Type: perfect trumpet. Floret type: solitary.

*Blooming habit.*—Upright and out facing 3 cm to 5 cm above foliage.

*Quantity of inflorescences per plant.*—40 to 60.

*Longevity of individual blooms on the plant.*—3 to 5 days.

*Immature inflorescence.*—Diameter, 1 cm to 2 cm. Color, upper surface RHS N89D ; midveins, RHS N89D ; lower surface, RHS N89D; mid-veins RHS N89D.

*Mature inflorescence.*—Floret horizontal diameter 5 cm to 7 cm. Vertical depth. 7 cm to 9 cm. Petal color: upper surface, RHS N89D with mid-veins and veining of RHS N89D; lower surface RHS N89D with mid-veins of RHS N89D.

*Corolla tube color.*—Inside, RHS N89D with veins RHS N89D, outside, RHS N89D with veins RHS N89D.

*Corolla tube length.*—2 cm to 3 cm.

*Corolla texture.*—Fine velvet.

*Calyx.*—Color, all surfaces variegated in ratios consistent with foliage. Length: 5 mm. Width: 2 mm. Shape: oblong. Apex shape: obtuse.

Figure 8:
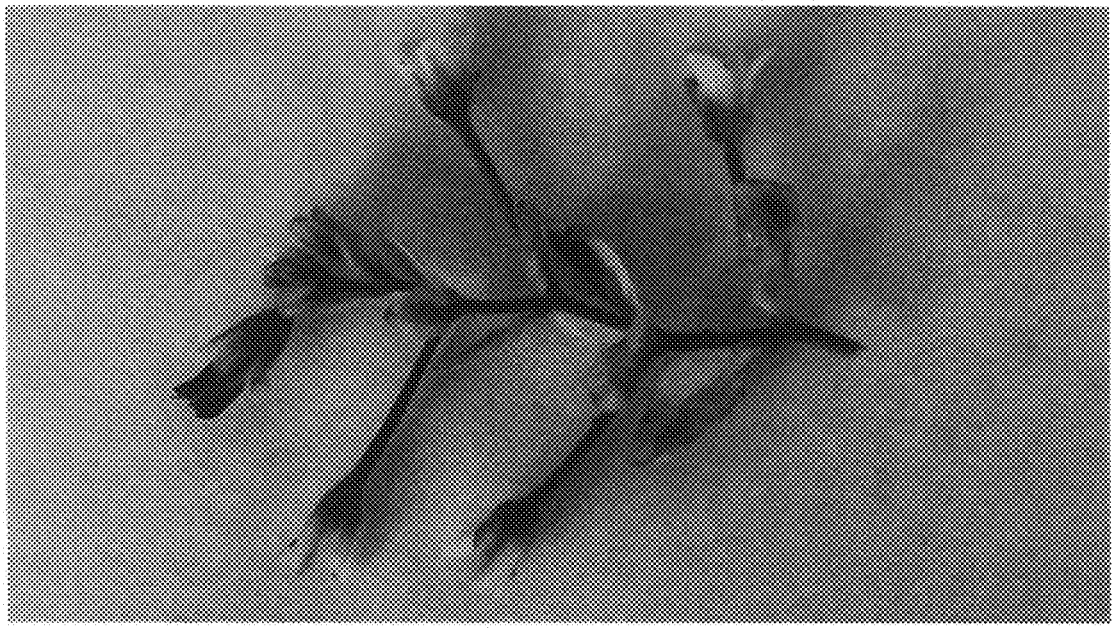
FIG. 8 is a photograph showing the branching habit of the new variety 'Drama Queen'.

*Floral arrangement.*—See FIG. 8.

*Base.*—Acute. Margin: entire. Texture, upper surface prunose and lower surface prunose.

*Pollen.*—RHS 116A in color.

*Fragrance.*—Sweet *petunia.*

*Bloom season.*—Late April through mid-October.

Disease/pest resistance: None noted, typical of other *petunias.*

We claim:

1. A new and distinct variety of *Petunia* plant substantially as illustrated and described herein.

* * * * *